US010213161B2

(12) United States Patent
Doerr (10) Patent No.: US 10,213,161 B2
(45) Date of Patent: Feb. 26, 2019

(54) IMPLANTABLE DEVICE WITH AN OXYGEN SENSOR AND A METHOD OF OPERATING AN IMPLANTABLE DEVICE WITH AN OXYGEN SENSOR

(71) Applicant: Biotronik SE & Co. KG, Berlin (DE)

(72) Inventor: Thomas Doerr, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 11 days.

(21) Appl. No.: 15/162,511

(22) Filed: May 23, 2016

(65) Prior Publication Data

US 2016/0338629 A1 Nov. 24, 2016

Related U.S. Application Data

(60) Provisional application No. 62/164,614, filed on May 21, 2015.

(51) Int. Cl.
*A61B 5/00* (2006.01)
*A61B 5/145* (2006.01)
(Continued)

(52) U.S. Cl.
CPC ............... *A61B 5/686* (2013.01); *A61B 5/01* (2013.01); *A61B 5/0245* (2013.01); *A61B 5/0422* (2013.01); *A61B 5/0538* (2013.01); *A61B 5/1107* (2013.01); *A61B 5/1459* (2013.01); *A61B 5/14539* (2013.01); *A61B 5/14552* (2013.01); *A61B 5/4836* (2013.01);
(Continued)

(58) Field of Classification Search
CPC .................................. A61N 1/686; A61N 1/01

USPC ........................................................... 607/18
See application file for complete search history.

(56) References Cited

U.S. PATENT DOCUMENTS 5,342,406 A 8/1994 Thompson
5,843,137 A 12/1998 Condle et al.
(Continued)

FOREIGN PATENT DOCUMENTS

EP 0793975 A2 9/1997
FR 2903912 A1 1/2008
(Continued)

OTHER PUBLICATIONS

European Search Report received from EP Application Serial No. 16166557.5, dated Mar. 21, 2017, 14 pages.
(Continued)

*Primary Examiner* — Nadia A Mahmood
(74) *Attorney, Agent, or Firm* — ARC IP Law, PC; Joseph J. Mayo (57) ABSTRACT

Embodiments include a method of determining an oxygen content in a bodily tissue or in blood of a human or animal body, wherein a variable representative of oxygen content in the bodily tissue or in the blood is detected at least over one cardiac cycle and is correlated with a contraction state of a heart. Embodiments include a device configured to be inserted into the human or animal body, wherein the device includes at least one sensor unit that detects a signal representative of an oxygen content along a measurement path. Embodiments include a reflector provided on the device, wherein the reflector is arranged in the measurement path between a transmitter and a receiver of the at least one sensor unit to reflect the signal.

16 Claims, 8 Drawing Sheets

(51) Int. Cl.
*A61B 5/01* (2006.01)
*A61N 1/39* (2006.01)
*A61B 5/0245* (2006.01)
*A61B 5/042* (2006.01)
*A61B 5/053* (2006.01)
*A61B 5/11* (2006.01)
*A61B 5/1455* (2006.01)
*A61B 5/1459* (2006.01)
*A61N 1/365* (2006.01)

(52) U.S. Cl.
CPC ......... *A61B 5/6869* (2013.01); *A61B 5/6882* (2013.01); *A61B 5/7246* (2013.01); *A61N 1/36557* (2013.01); *A61N 1/3987* (2013.01); *A61B 5/1118* (2013.01); *A61B 2560/0252* (2013.01); *A61B 2562/0238* (2013.01)

(56) References Cited

U.S. PATENT DOCUMENTS

| | | |
|---|---|---|
| 7,267,649 B2 | 9/2007 | Zdeblick et al. |
| 2006/0247702 A1 | 11/2006 | Stegemann et al. |
| 2007/0239052 A1* | 10/2007 | Bhunia ............ A61B 5/02028 600/513 |
| 2007/0239215 A1 | 10/2007 | Bhunia et al. |
| 2010/0022856 A1 | 1/2010 | Cinbis et al. |
| 2010/0030043 A1 | 2/2010 | Kuhn |
| 2010/0198284 A1 | 8/2010 | Zhou et al. |
| 2010/0280348 A1 | 11/2010 | Wenzel et al. |
| 2011/0009754 A1 | 1/2011 | Wenzel et al. |
| 2011/0190610 A1 | 8/2011 | Kuhn et al. |
| 2013/0289372 A1 | 10/2013 | Imran |

FOREIGN PATENT DOCUMENTS

| | | |
|---|---|---|
| WO | 9616696 A1 | 6/1996 |
| WO | 2004066814 A2 | 8/2004 |
| WO | 2010088539 A1 | 8/2010 |

OTHER PUBLICATIONS

European Search Report received from EP Application Serial 16166557.5, dated Nov. 11, 2016, 8 pages.

* cited by examiner

FIG. 10

IMPLANTABLE DEVICE WITH AN OXYGEN SENSOR AND A METHOD OF OPERATING AN IMPLANTABLE DEVICE WITH AN OXYGEN SENSOR This application claims the benefit of U.S. Provisional Patent Application 62/164,614 filed on 21 May 2015, the specification of which is hereby incorporated herein by reference.

BACKGROUND OF THE INVENTION

Field of the Invention

Embodiments of the invention generally relate to an implantable device including an oxygen sensor, and a method of operating an implantable device that includes an oxygen sensor.

Description of the Related Art

Generally, oxygen sensors for implantation into the human or animal body are used for the measurement of the oxygen content in the blood, i.e. in cavities filled with blood, such as heart ventricles or blood vessels, and in the tissue with a blood supply. Typically, optical sensors may include three arrangements. In the case of the transmitted light method, generally, the blood or tissue is arranged between a source and a detector. In the case of the scattered light method, typically, the source radiates light into the tissue or blood, and the detector uses the reflected spectrum. In the case of the reflection method, generally, a mirror reflects the light emitted by the source onto the detector, and the blood or tissue to be examined is located in the two light paths— source/mirror and mirror/detector. For example, United States Patent Application Publication 20130289372 A1, entitled "Implantable Oximetric Measurement Apparatus and Method of Use", to Imran, appears to disclose an apparatus, system, kit and method for in vivo measurement of blood oxygen saturation. In addition, for example, United States Patent Application Publication 20070239215 A1, entitled "Method and Apparatus for Using an Optical Hemodynamic Sensor to Identify an Unstable Arrhythmia", to Bhunia et al., appears to disclose a medical device that identifies a hemodynamically instable arrhythmia based upon optical hemodynamic sensor signals. For example, Untied States Patent Application Publication 20070239052 A1, entitled "Method and Apparatus for Verifying a Determined Cardiac Event in a Medical Device Based on Detected Variation in Hemodynamic Status", to Bhunia, appears to disclose detecting variations in hemodynamic status that includes a physiologic sensor sensing physiologic signals to generate a plurality of variation index samples corresponding to the sensed signals. In addition, for example, United States Patent Application Publication 20110190610 A1, entitled "Optical Sensor for Medical Device", to Kuhn et al., appears to disclose a fixed lens spacing between emit and receive modules to achieve target sensor sensitivity, while varying other sensor parameters in order to increase signal amplitude without increasing power demand.

In view of the above, there is a need for a simple and reliable permanently implantable device, wherein oxygen content in the blood or tissue may be determined.

In addition, in view of the above, there is a need for a method and a device that determine the oxygen extraction rate of the heart, which allows for a quick-acting therapeutic measure.

BRIEF SUMMARY OF THE INVENTION

Objectives of one or more embodiments of the invention are achieved in accordance with the features of the independent claims. In addition, at least one embodiment of the invention will emerge from the other claims, the description, and the drawings.

At least one embodiment of the invention includes a device that may be inserted into the human or animal body. In one or more embodiments, the device may include at least one permanently implantable sensor unit that detects a signal representative of an oxygen content along a measurement path, wherein the at least one permanently implantable sensor unit includes a transmitter and a receiver. In at least one embodiment, a reflector may be provided on the device, wherein the reflector is arranged between the transmitter and the receiver of the sensor unit to reflect the signal in the measurement path.

In one or more embodiments of the invention, various suitable equivalent variables dependent on a current oxygen content in bodily tissue or blood may be used to detect oxygen in the tissue or in the blood. At least one embodiment may include transmission and/or absorption of electromagnetic signals in a given frequency range, such as in an infrared or optical frequency range. In one or more embodiments, the additional term "optical" may relate to both the visible range and to the infrared range of the electromagnetic frequency spectrum. In one or more embodiments, the sensor unit may be or may include an optical sensor unit, such as an oximeter, which functions in a frequency range between 600 nm and 1000 nm, for example between 660 nm and 940 nm. In at least one embodiment, the receiver may be formed by or may include an oximeter formed of or including one or more light-emitting or laser diodes and a phototransistor, a photodiode or a photoresistor. In one or more embodiments, a red and an infrared light source may be used to determine the local oxygen saturation in the measurement path.

By way of one or more embodiments, the device provides an improvement to the treatment of cardiac insufficiency patients. Typically, prior art devices and methods primarily take into consideration a maximum cardiac output as an optimization target. However, at least one embodiment of the invention includes myocardial oxygen consumption in the form of an oxygen extraction rate in defined load situations and improve such an oxygen extraction rate to the greatest possible extent. As such, in one or more embodiments, progression of the cardiac insufficiency to decompensation may be avoided or at least delayed. In at least one embodiment, blood supply of a left ventricle in a region of sub-myocardial coronary arteries may be heavily reduced by perfusion during systole, since the coronary vessel is heavily compressed by the contraction of the working musculature and is therefore predominantly closed. With increasing heart rate, in one or more embodiments, temporal proportion of the left-ventricular systole in relation to a total cardiac cycle also rises. According to at least one embodiment of the invention, the device may permanently monitor myocardial oxygen balance, such that a drug and/or electrical therapy may be adapted to the respective cardiac state. In one or more embodiments, one or more of stimulation frequency of a cardiac pacemaker may be reduced, a power of a heart assist pump may be increased, a cardiac contractility modulation (CCM) stimulation may be activated, a dosing of a beta-blocker or other drugs may be adapted, and in extended emergency systems dobutamine may be administered automatically.

In at least one embodiment, the myocardial oxygen extraction rate includes a difference, in the form of a percentage, of the oxygen content between coronary arteries and coronary veins. With decreasing oxygen availability, in one or more embodiments, the oxygen extraction rate initially increases, until the tissue-typical maximum thereof is reached. From this point, in at least one embodiment, the onset of tissue hypoxia with resultant decompensation is assumed. In one or more embodiments, the device may identify this point and provide therapeutic intervention in a timely manner.

In at least one embodiment, the implantable sensor may continuously monitor the myocardial oxygen extraction rates, such as in cardiac insufficiency patients, and may adapt the therapy requirements accordingly. In one or more embodiments, tissue oxygen saturation may be determined in an uninterrupted manner. In at least one embodiment, electronic implants may be coupled functionally and/or structurally to the device and may be used to provide diagnostics or to provide therapy management.

One or more embodiments may include permanently implantable monitoring of the myocardial oxygen balance (oxygen extraction rate) to monitor progress and to provide therapy management in cardiac insufficiency patients.

In at least one embodiment of the invention, the reflector may be arranged on or in a fixation unit to permanently fix the device to or in a bodily tissue. In one or more embodiments, various fixing mechanisms to fix the device to a tissue structure may be used. In at least one embodiment, the device may be fixed permanently on or in the bodily tissue. In one or more embodiments, one or more assemblies used to measure oxygen content, oxygen saturation, oxygen extraction rate and/or other measurements may be suitably positioned and fixed, without further additional implantation steps. In at least one embodiment, the fixation unit may be or may include a helix to permanently fix the electrode line in the bodily tissue. In one or more embodiments, a part of, or the entire fixation unit, may be mirrored or polished, providing an additional reflector for the signals which the transmitter sends to the receiver in order to perform an oxygen-sensitive measurement, such as an oxygen saturation measurement.

In at least one embodiment, the sensor unit may be coupled to one or more therapeutic implants. In one or more embodiments, the measured values of the sensor unit may be evaluated and/or assessed using an evaluation unit, such that critical ranges of an oxygen extraction rate and/or an oxygen saturation may be identified.

In at least one embodiment of the invention, the device may include the sensor unit and a therapy unit coupled to the sensor unit. In one or more embodiments, the sensor unit may be part of a therapy unit that includes one or more of at least one sensing electrode, at least one therapeutic stimulation electrode, and at least one defibrillation electrode. In at least one embodiment, if a critical measured value or range is identified, a therapeutic measure may be taken via the therapy unit.

In at least one embodiment, the sensor unit may be coupled to an arrangement that detects a pH value. In one or more embodiments, the arrangement may be integrated into the sensor unit. In at least one embodiment, the pH value may additionally be determined, and wherein oxygen saturation values in the bodily tissue or in the blood may be corrected accordingly. As such, in one or more embodiments, measurement accuracy may be increased.

In at least one embodiment, the sensor unit may be coupled to a temperature sensor or to both a temperature sensor and a heating element. In one or more embodiments, temperature-dependent effects in the region of the measurement path, which may falsify the measurement results, may be compensated by using a temperature sensor. In at least one embodiment, the temperature sensor may be a thermistor, a thermocouple, a P-N diode, a bipolar transistor, or the like.

One or more embodiments may include a heating element, wherein a defined temperature in the region of the measurement path may be set in order to eliminate temperature effects during the measurement. In at least one embodiment, a region of the bodily tissue may be heated selectively. In one or more embodiments, a number of individual elements may be distributed over a wide region in order to achieve a temperature distribution that is as constant as possible. In at least one embodiment, the heating element may be or may include a heating resistor for example, which may be controlled or regulated in order to avoid an undesirable overheating of the bodily tissue or an influencing of the electronics of the device or of other implants. In one or more embodiments, the heating element may be arranged for example on a housing of the device or on another implant.

By way of at least one embodiment, by heating the bodily tissue, a selected vessel expansion may be provoked, for example in order to selectively increase an arterial contribution to local determination of the oxygen content. In one or more embodiments, arterial, venous and capillary blood volumes in the bodily tissue may contribute to the measurement. With some measurements, in at least one embodiment, arterial or venous contributions may be undesirable, for example with the measurement of the oxygen content in the skeletal muscles.

In at least one embodiment, the sensor unit may be coupled to an arrangement that detects a contraction state of bodily tissue in the region of the measurement path. In one or more embodiments, the arrangement that detects the contraction state may detect a mechanical contraction state and for example may include one or more strain gauges, one or more pressure sensors, and/or one or more acceleration sensors. In at least one embodiment, a temperature measurement may be used in order to determine the contraction state. In one or more embodiments, heart sounds may be used in order to determine the contraction state. One or more embodiments may include a combination of two or more of the methods discussed herein in order to increase the measurement accuracy. In at least one embodiment, the detection of the mechanical contraction state of the heart may be used to distinguish between systole and diastole. In one or more embodiments, the mechanical contraction state may be detected using a unipolar, continuous impedance measurement in order to determine from these signals the start and end of the contraction states. In at least one embodiment, the detection of the mechanical contraction state may be performed in a classification unit. In one or more embodiments, the sensor unit may be coupled to the arrangement that detects the contraction state or may include the arrangement that detects the contraction state, such that the signal responding to an oxygen content may be associated with a certain contraction state. In at least one embodiment, phases of a mechanical pumping function of the heart may be associated over time with the oxygen saturation, which may be performed in a synchronization unit. In one or more embodiments, the oxygen profile with respect to a hypoxia criterion, for example excessive decrease at the end of the systole based on the average oxygen value over the entire cardiac cycle, may be evaluated therefrom in an evaluation unit and may be signaled.

In at least one embodiment, the sensor unit may be connected to an electrode line to sense the electrical activity of the heart to determine the cardiac cycle length. In one or more embodiments, the signal representative of an oxygen content may be determined for a cardiac cycle and/or certain phases of a cardiac cycle. At least one embodiment may include detection of the electrical activity of the heart to distinguish between systole and diastole.

In at least one embodiment of the invention, a maximum myocardial oxygen saturation, a minimum myocardial oxygen saturation, and a difference between minimum and maximum myocardial oxygen saturation may be determined from the signal representative of an oxygen content, and therefrom an oxygen extraction rate of the heart may be derived.

In at least one embodiment of the invention, from the signal representative of an oxygen content, the maximum, minimum, and the difference of the myocardial oxygen saturation over a cardiac cycle may be determined, and therefrom a course of an oxygen extraction rate may be determined dependent from the heart rate.

In at least one embodiment, a critical point of the oxygen extraction rate may be determined from a course of the measured oxygen extraction rate over the heart rate, for example when one or more of the oxygen extraction rate decreases with rising heart rate; the oxygen extraction rate with rising heart rate transitions into a saturation range; and the oxygen extraction rate with rising heart rate transitions into a saturation range and at the same time the maximum oxygen saturation value decreases.

In one or more embodiments of the invention, a critical point of the oxygen extraction rate may be determined, for example when a systolic oxygen saturation falls below a critical reference value or the rate of decrease exceeds a critical value during the systole.

At least one embodiment of the invention may include a cardiac assist system including a device that includes at least one permanently implantable sensor unit that detects a signal representative of an oxygen content along a measurement path of the sensor unit. In at least one embodiment, the sensor unit may include a transmitter and a receiver. In one or more embodiments, the device may include at least one therapy unit, and a control unit. One or more embodiments may include a reflector on the device, wherein the reflector may be arranged in a measurement path between the transmitter and the receiver of the sensor unit to reflect the signal. In at least one embodiment, the control unit may optimize one or more stimulation and/or therapy parameters, such that an oxygen saturation in the region of the measurement path with respect to a defined state of load of the heart may be set.

In one or more embodiments, the device may be constructed as described above.

In at least one embodiment, the sensor unit may be coupled to an arrangement that detects a contraction state of the heart.

In at least one embodiment, one or more stimulation and/or therapy parameters may be optimized such that an oxygen saturation with respect to a defined state of load of the heart is set.

One or more embodiments of the invention may include a method of determining an oxygen content in a bodily tissue or in the blood of a human or animal body, wherein a variable representative of an oxygen content in the tissue or in the blood may be detected at least over one cardiac cycle and may be correlated with a contraction state of the heart.

In at least one embodiment, the method may include determining a maximum myocardial oxygen saturation, a minimum myocardial oxygen saturation, and a difference between minimum and maximum myocardial oxygen saturation from the oxygen-dependent variable, and therefrom deriving an oxygen extraction rate of the heart.

In at least one embodiment, the method may include determining the maximum, minimum, and the difference of the myocardial oxygen saturation over a cardiac cycle from the measured oxygen-dependent variable, and therefrom determining a course of an oxygen extraction rate dependent from the heart rate.

In at least one embodiment, the method may include determining a critical point of the oxygen extraction rate from the course of the measured oxygen extraction rate over the heart rate, wherein the critical point may include one or more of when the oxygen extraction rate decreases with increasing heart rate; when the oxygen extraction rate with increasing heart rate transitions into a saturation range; and when the oxygen extraction rate with increasing heart rate transitions into a saturation range and at the same time the maximum oxygen saturation value decreases.

In one or more embodiments, the measurement may be performed with a sensor unit, as described above with the device that may be inserted into the human or animal body, including a sensor unit that includes at least one permanently implantable sensor unit to detect a signal representative of an oxygen content along a measurement path. As described above, in at least one embodiment, a reflector may be provided on the device, wherein the reflector may be arranged in the measurement path between the transmitter and the receiver of the sensor unit to reflect the signal. By way of at least one embodiment, other suitable devices and/or sensor units may be used.

In one or more embodiments, with decreasing oxygen availability, the oxygen extraction rate initially increases, until the tissue-typical maximum thereof is reached. Therefrom, in at least one embodiment, the onset of tissue hypoxia with resultant decompensation may be assumed.

In at least one embodiment, a critical point may be determined, for example when a systolic oxygen saturation falls below a critical reference value or the rate of decrease exceeds a critical value during the systole.

In at least one embodiment, one or more stimulation and/or therapy parameters may be optimized such that an oxygen saturation with respect to a defined state of load of the heart may be set. In one or more embodiments, the device that includes the sensor unit may be connected to a suitable evaluation unit to optimize the one or more stimulation and/or therapy parameters. In at least one embodiment, the critical point of the measured oxygen extraction rate may be determined, for example via the evaluation unit, when the oxygen extraction rate decreases with rising heart rate. In one or more embodiments, the critical point of the measured oxygen extraction rate may be determined, for example via the evaluation unit, when the oxygen extraction rate with rising heart rate transitions into a saturation range. In at least one embodiment, the evaluation unit may determine the critical point of the measured oxygen extraction rate when the oxygen extraction rate transitions with rising heart rate into a saturation range and at the same time the maximum oxygen saturation value decreases. In one or more embodiments, the evaluation unit may determine the maximum, minimum, and the difference of the myocardial oxygen saturation over a cardiac cycle and may record the course of this oxygen extraction rate determined in a manner based on heart rate. In at least one embodiment, a trend from the differential values may be determined, such that therapeutic measures may be taken as necessary.

By way of one or more embodiments, the evaluation unit may be connected to an electrode line in order to sense the electrical activity of the heart and to determine the cardiac cycle length.

One or more embodiments of the invention may monitor the myocardial oxygen supply in a permanently implantable device, may identify the moment in time of the onset of myocardial hypoxia, such as in cardiac insufficiency patients, and may automatically or manually adapt the therapy.

BRIEF DESCRIPTION OF THE DRAWINGS

The above and other aspects, features and advantages of at least one embodiment of the invention will be more apparent from the following more particular description thereof, presented in conjunction with the following drawings, wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

The figures are schematic illustrations of one or more embodiments of the invention, wherein functionally identical or identically acting elements are each designated by the same reference signs.

Figure 1:
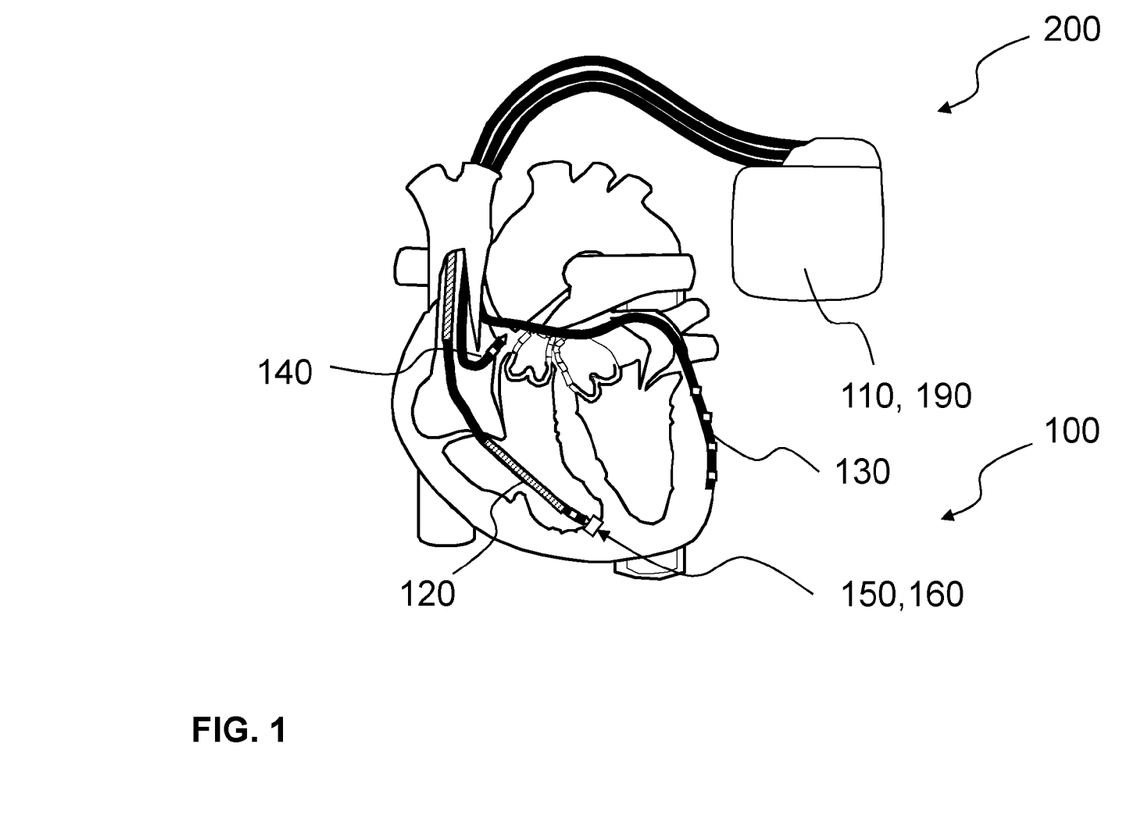
FIG. 1 shows a schematic illustration of a section through a heart including a permanently implanted device according to one or more embodiments of the invention, wherein the device is integrated in a cardiac assist system.

FIG. 1 shows a section through a heart having a device 100, according to one or more embodiments of the invention, implanted permanently into a human or animal body, wherein the device may be integrated in a cardiac assist system 200. In at least one embodiment, the device 100 may include at least one sensor unit 150, wherein the at least one sensor unit 150 may detect a signal representative of an oxygen content along a measurement path 160 of the sensor unit 150, which is illustrated in greater detail by way of example in FIGS. 2 and 3.

In one or more embodiments, the cardiac assist system 200 may include a pulse generator 110 with a control unit 190, to which a right-ventricular sensing, stimulation and shock electrode line 120, a left-ventricular quadrupole sensing and stimulation electrode line 130, and an atrial sensing and stimulation electrode line 140 are connected. In at least one embodiment, the electrical supply of the cardiac assist system 200 may be integrated in the pulse generator 110 or may be provided externally. In one or more embodiments, the sensor unit 150 may be arranged in the electrode head at the distal end of the right-ventricular sensing, stimulation and shock electrode line 120. In at least one embodiment, the sensor unit 150 may include or may be formed by an optical myocardial oximeter sensor that includes a LED phototransistor system with a transmitter and a receiver, shown as transmitter 152 and receiver 154 in FIGS. 2 and 3.

By way of one or more embodiments, the sensor unit 150 may be arranged at the distal end of the right-ventricular electrode line 120 such that the sensor unit 150 may determine, after implantation of the electrode, for example exclusively, the myocardial oxygen saturation. In at least one embodiment, the LED phototransistor system may be arranged such that, after implantation, it may irradiate only into the myocardium and may detect the corresponding reflection. In one or more embodiments, the transmitter 150 may be or may include oximeters formed of two LEDs with a wavelength of 660 nm and 940 nm, and the receiver 154 may be or may include a phototransistor. By way of one or more embodiments, the transmitter and receiver structures may be accommodated in the electrode head using various integration methods.

As shown in FIG. 1, the cardiac assist system 200 may be or may include a cardiac resynchronization therapy system with a defibrillator (CRT-D), according to one or more embodiments of the invention. In at least one embodiment, the cardiac assist system 200 may be or may include a cardiac resynchronization therapy system with a pacemaker (CRT-P), or may be or may include a ventricular assist device (VAD) system. In one or more embodiments, the VAD system may include a ventricular assists system that takes on part of, or all of, the pumping function of the heart. In at least one embodiment, the cardiac assist system 200 may be or may include a cardiac contractility modulator (CCM) stimulator, such as a cardiac contractility modulator that stimulates the heart muscle with non-exciting electrical signals. In one or more embodiments, the cardiac assist system 200 may be or may include an aortic balloon pump. Embodiments of the invention may include combinations of two or more of the various systems discussed above as cardiac assist system 200.

Figure 2:
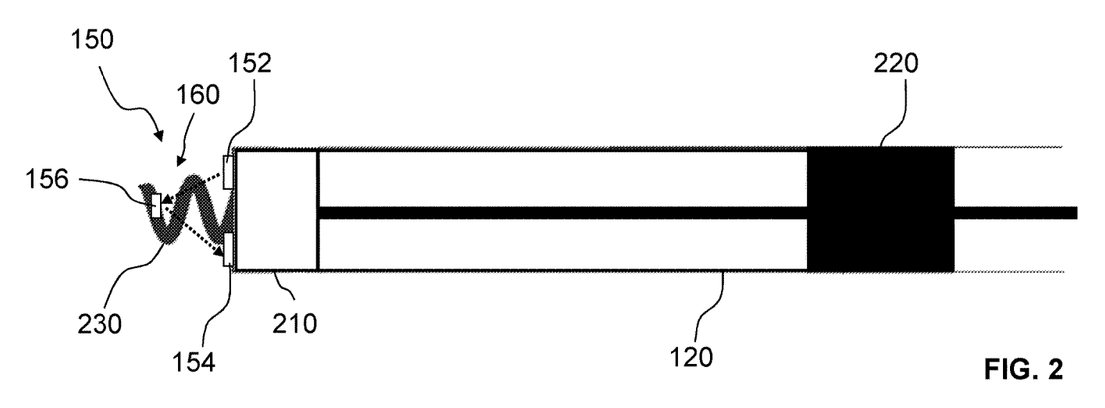
FIG. 2 shows a schematic illustration of a section through an electrode head including a sensor unit with a transmitter and a receiver, and a reflector on a fixation unit of the electrode head.
Figure 3:
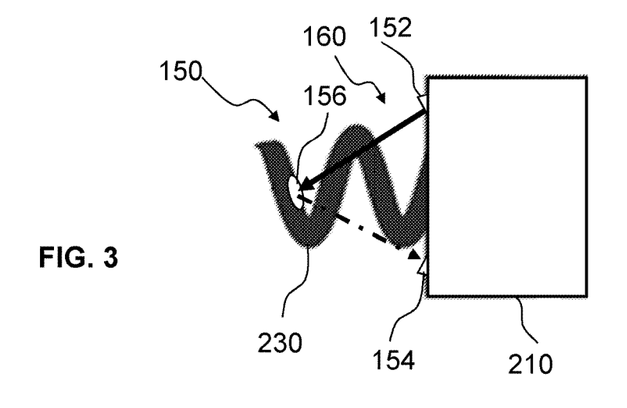
FIG. 3 shows a schematic illustration of a detail of the electrode head of FIG. 2.

FIG. 2 shows a section through a distally arranged electrode head of the right-ventricular electrode line 120 from FIG. 1 with the sensor unit 150, which may include an optical unit, according to one or more embodiments of the invention. FIG. 3 shows a detail of the electrode head from FIG. 2, according to one or more embodiments of the invention. In at least one embodiment, the electrode head may include electrode poles, such as a tip electrode 210 and/or one or more ring electrodes 220. In one or more embodiments, the electrode 120 shown in FIGS. 2 and 3 may include a helix 230 to permanently fix the electrode line 120 in the bodily tissue, such as in the myocardium. In at least one embodiment, alternatively or additionally to the tip electrode 210, the helix 230 may be used as an electrode pole. In one or more embodiments, the distal end of the electrode 120 may be equipped with or may include two LEDs as transmitter 152 and a phototransistor as receiver 154, which together provide an optical oximeter that detects the tissue along the measurement path 160. By way of at least one embodiment, to be able to operate the system in a reliable manner with minimum power, part of the fixation unit or the entire fixation unit may be mirrored or polished, such that the device may additionally include a reflector 156 for the red and infrared beams to measure the oxygen saturation along the measurement path 160.

In one or more embodiments, alternatively or in addition to a helix 230, other anchoring devices may be used to fix the electrode line in the bodily tissue, such as a barbed hook or the like.

In at least one embodiment, with the reflector 156, the device may only predominantly determine the myocardial oxygen.

FIG. 3 illustrates the electrode head from FIG. 2 in an enlarged manner according to one or more embodiments of the invention. In at least one embodiment, the housing of the electrode head may include the fixation helix 230 as a rigid helix or as a helix that may be unscrewed. In one or more embodiments, for the optical oximeter, one or more LEDs may be positioned as transmitter 152 on the electrode head such that the one or more LEDs direct their focus onto a polished surface of the fixation helix 230. In at least one embodiment, the polished surface may form the reflector 156 on the helix 230 and may be arranged such that, in the unscrewed state, the reflector 156 may reflect the light onto the phototransistor serving as receiver 154 and therefore provide a robust measurement of blood oxygen.

One or more embodiments may include a unit that determines the pH value, for example at the same time, and the measured variable representing the oxygen content, for example an optical signal representing the oxygen saturation, may be corrected accordingly. In at least one embodiment, the pH value compensation may be used in applications having a high signal resolution. In at least one embodiment, the Bohr effect may be used to describe a pH-dependent oxygen binding capacity of the blood. In one or more embodiments, with a decreasing pH value, the oxygen binding in the blood also decreases.

In one or more embodiments, the sensor unit 150 may be used for various applications.

According to at least one embodiment, the sensor unit 150 may be used to time cardiac resynchronization therapy (CRT), such as oximeter-controlled CRT timing, in which for an implantable cardiac stimulator, such as a CRT stimulator, the stimulation parameters are optimized based on a myocardial oxygen saturation measurement using the sensor unit 150. In one or more embodiments, the oxygen saturation may be determined over a total cardiac cycle. In at least one embodiment, the optimization may set a minimum difference between maximum and minimum myocardial oxygen saturation $SpO_2$ with defined cardiac output.

In one or more embodiments, the sensor unit 150 may control defibrillation, such as an oximeter-controlled defibrillation, in which, based on the measured myocardial oxygen saturation or a course thereof from the onset of a primary frequency-detected tachycardia, the moment in time of the defibrillation shock delivery may be determined. As such, in at least one embodiment, the shock therapy may then always or only be delivered when the myocardial oxygen saturation has fallen below a certain limit value or percentage.

In one or more embodiments, the sensor unit 150 may be used to adjust oximeter-controlled frequency and/or may be used to avoid unnecessary stimulation in the case of leadless pacemakers, such as an injectable leadless pacer (iLP) or a leadless pacer (LLP). In at least one embodiment, the iLP or the LLP may be equipped with a sensor unit 150, wherein the iLP or LLP may deliver a stimulation as a back-up pacemaker when the measured myocardial oxygen saturation has fallen below a critical value (absolutely or relatively, measured over the cardiac cycle) or, optionally, when a very long RR interval is exceeded. In one or more embodiments, the RR interval is the distance between two R waves, which appear in an electrocardiogram as spikes and define the temporal distance between two heartbeats, i.e. between the start of two contractions of the heart ventricles. In at least one embodiment, with a rate-adaptive leadless pacemaker, the maximum stimulation frequency may be limited depending on the myocardial oxygen saturation by reducing the stimulation frequency with high and possibly long-lasting high stimulation frequencies with decreasing oxygen saturation. At least one embodiment may include a second sensor that signals the metabolic need, to adapt the rate, such as an activity sensor, which may specify higher stimulation frequencies. In one or more embodiments, pacemaker-induced decompensation may be avoided.

By way of at least one embodiment, therapy may be optimized with the device 100 that includes the sensor unit 150, wherein a continuous measurement over a physiological cycle may be measured, for example over a cardiac cycle, a respiratory cycle and the like. In one or more embodiments, due to the coupling with one or more therapeutic implants and/or one or more further sensor implants, a therapeutic measure and/or stimulation may be provided individually and in a precise manner. In at least one embodiment, the measured oximeter data may be sent via an automatic telemetry system to one or more of a doctor, the patient, other individuals, and to an automatic evaluation system.

In one or more embodiments, due to the coupling of the sensor unit 150 to the control unit 190, shown in FIG. 1, one or more stimulation and/or therapy parameters may be optimized such that an optimal oxygen saturation with respect to a defined state of load, for example heart rate, of the heart is set.

By way of at least one embodiment, the sensor unit 150 may be coupled additionally or alternatively to an arrangement that detects a contraction state of bodily tissue in the region or in the surroundings of the measurement path 160. For example, in one or more embodiments, the contraction state of the heart may be detected directly and correlated with the measurement signal of the sensor unit 150.

In at least one embodiment, an optimization may be performed for example via a modulation of the atrioventricular (AV) time, (atrioventricular conduction time), which describes the period of time in which an excitation of the sinoatrial node spreads over the atria to the heart ventricles. In one or more embodiments, an optimization may be performed via a modulation of the ventriculo-ventricular (VV) time, which describes the temporal delay between right-ventricular and left-ventricular stimulation. In at least one embodiment, an optimization via a variation of the stimulation location and/or the stimulation polarity may be provided. In one or more embodiments, an optimization via a modulation of the stimulation frequency may be provided.

In one or more embodiments, the device 100 with sensor unit 150 may be coupled to a temperature sensor and/or a heating element (not illustrated). As such, in at least one embodiment, a correction of temperature influences with the measurement of signals representative of an oxygen content along a measurement path 160 may be provided. In one or more embodiments, a predefined temperature may be set and a variable temperature influence during the measurement may be ruled out. In at least one embodiment, with an incremental change of the temperature during the measurement, identification of an unusual response to a temperature change may be determined and examined. In one or more embodiments, the blood oxygen saturation may rise by 0.5% with a temperature increase of 2° C.

In at least one embodiment, a vessel may expand as a result of a selected local temperature increase, such that contributions to the measurement signal from various regions may be selectively emphasized or suppressed.

In at least one embodiment of the invention, the sensor unit 150 may be coupled to a heating element, a temperature sensor and one or more stimulation electrodes. In one or more embodiments, the heating element and temperature sensor may be positioned between the transmitter 152 and the receiver 154, wherein the transmitter 152 and the receiver 154 may be positioned in a compact arrangement between two or more stimulation electrodes arranged closely together (for example between a ring electrode and fixation helix or tip electrode and fixation helix). In at least one embodiment, the stimulation electrodes may be connected to an appropriate electronics unit to selectively emit stimulation pulses.

According to one or more embodiments of the invention, the method of determining an oxygen content in a bodily tissue or in the blood of a human or animal body may include detecting an oxygen-dependent variable with respect to an oxygen content in the tissue or in the blood at least over one cardiac cycle. In at least one embodiment, the oxygen-dependent variable that is detected may be correlated with a contraction state of the heart. FIGS. 1 to 3 illustrate a device with a sensor unit, by way of one or more embodiments, however other devices and/or sensor units may be used while keeping within the scope of the invention.

In at least one embodiment, a maximum myocardial oxygen saturation, a minimum myocardial oxygen saturation, and a difference between minimum and maximum myocardial oxygen saturation may be determined from the oxygen-dependent variable, and therefrom an oxygen extraction rate of the heart may be derived.

In one or more embodiments, the oxygen extraction rate may be determined using an implantable myocardial oxygen sensor, which is connected to an evaluation unit. In at least one embodiment, with respect to various cardiac function states, for example frequency, AV times, intrinsic VV times or QRS signal width, ventricular extrasystoles (VES), ventricular tachycardia (VT), and atrial fibrillation (Afib), the evaluation unit may determine at least the difference between maximum and minimum oxygen saturation $SpO_2$ and therefrom may conclude the myocardial extraction rate. As such, in one or more embodiments, the progress of patients with chronic coronary heart disease and limited pumping function may be monitored.

Figure 4:
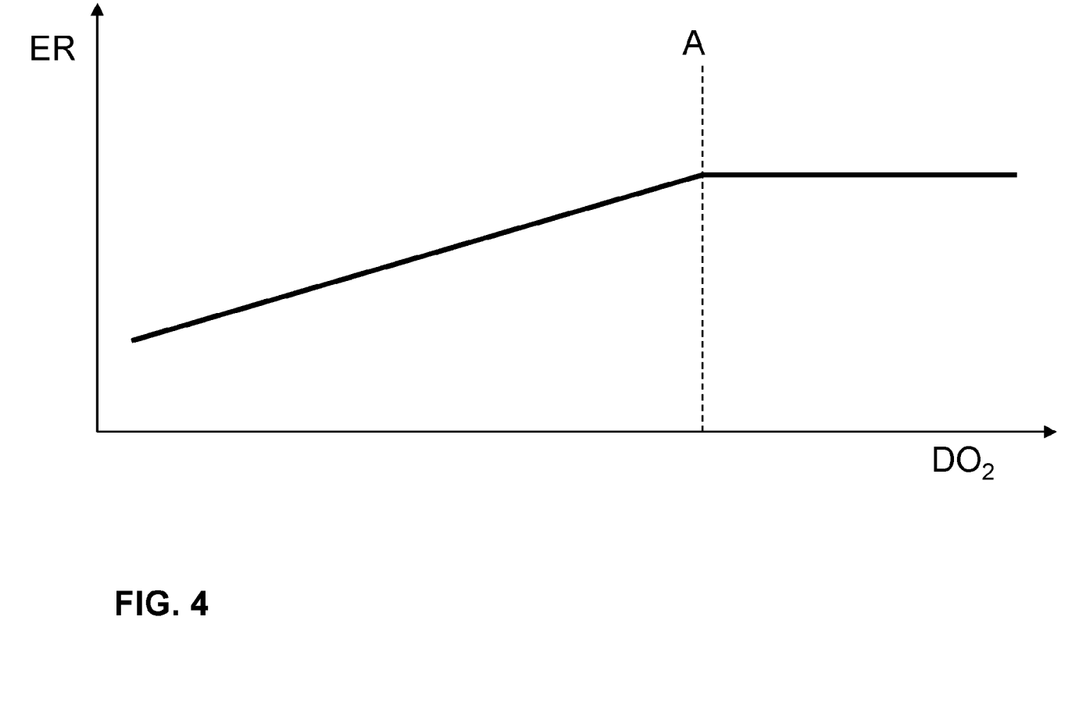
FIG. 4 shows a schematic illustration of a course of a myocardial oxygen extraction rate dependent from a decreasing oxygen availability.

FIG. 4 shows a course of a myocardial oxygen extraction rate ER depending on a decreasing oxygen availability $DO_2$, wherein the oxygen availability $DO_2$ decreases from left to right in the figure, according to one or more embodiments of the invention. In at least one embodiment, with decreasing oxygen availability $DO_2$, the extraction rate ER initially rises, until a tissue-typical maximum A is reached. In one or more embodiments, the extraction rate ER then remains constant.

Figure 5:
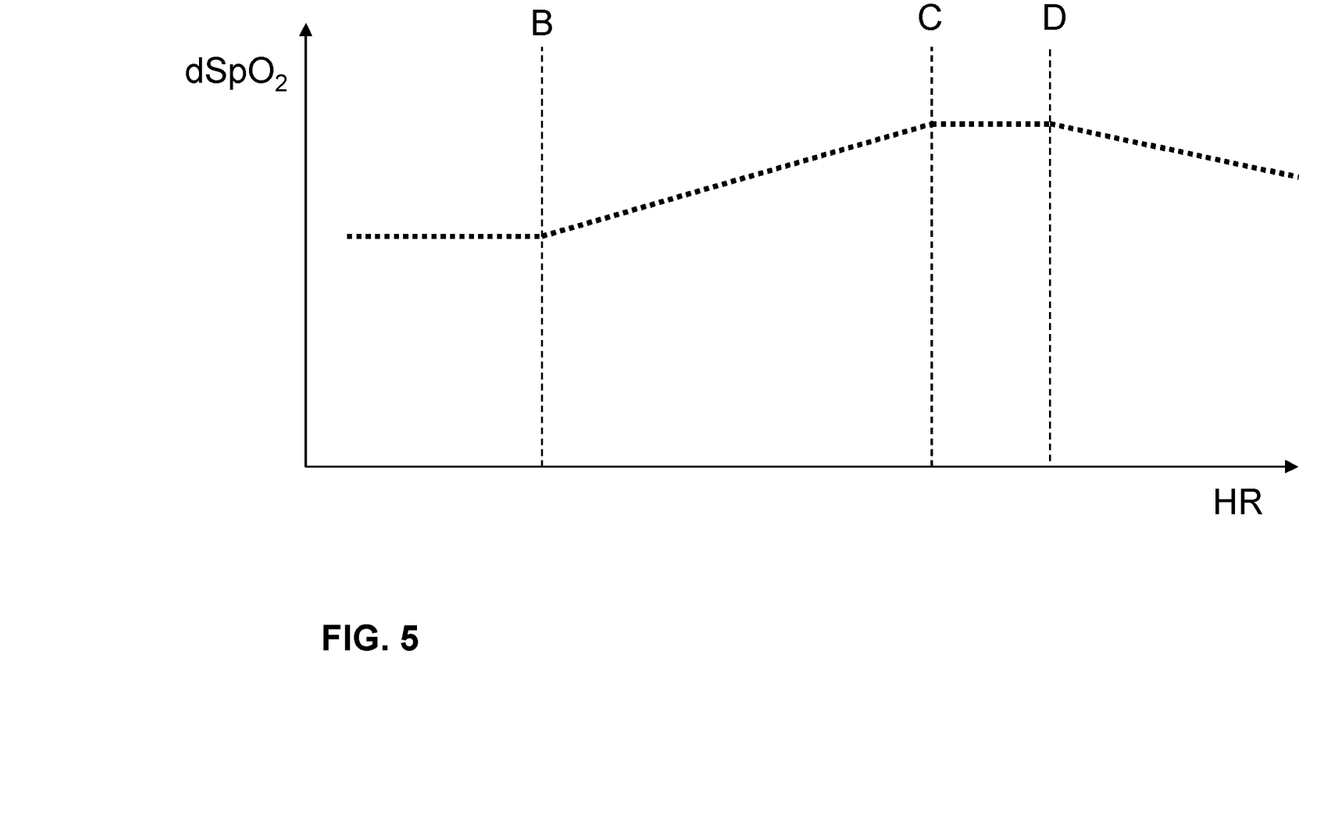
FIG. 5 shows a schematic illustration of a course of an oxygen extraction rate measurand dependent from a heart rate.

FIG. 5 shows a course of an oxygen extraction rate measurand $dSpO_2$ depending on the heart rate HR, wherein the heart rate HR increases from left to right in the figure, according to one or more embodiments of the invention. In at least one embodiment, the measurand shown in FIG. 5 is the difference between the minimum and the maximum tissue oxygen saturation $SpO_2$ in the myocardium, for example measured using a tissue oxygen sensor, as described in FIGS. 1 to 3.

In one or more embodiments, with increasing heart rate HR, the oxygen availability may increase as a result of increased coronary perfusion, wherein the measurand remains approximately constant up to a heart rate B, for example wherein the extraction rate $dSpO_2$ also does not increase. In at least one embodiment, if the oxygen availability starts to stagnate based on the cardiac insufficiency with further heart rate increase (B), an increase of the extraction rate $dSpO_2$ may lead to an increase of the measurand. In one or more embodiments, when the maximum myocardium oxygen extraction rate is reached (point C in the figure), a plateau in the measurand may be recorded with further increasing heart rate HR. In at least one embodiment, the plateau between the values C and D of the heart rate HR may be interpreted as a signal of myocardial hypoxia. In one or more embodiments, with further increasing heart rate HR or phases of long-lasting high heart rate HR, the coronary perfusion may decrease on account of the increasingly restricted pumping performance, caused by the hypoxia, and the measurand may also start to decrease. In at least one embodiment, such a phase may signal an acute decompensation.

Figure 6:
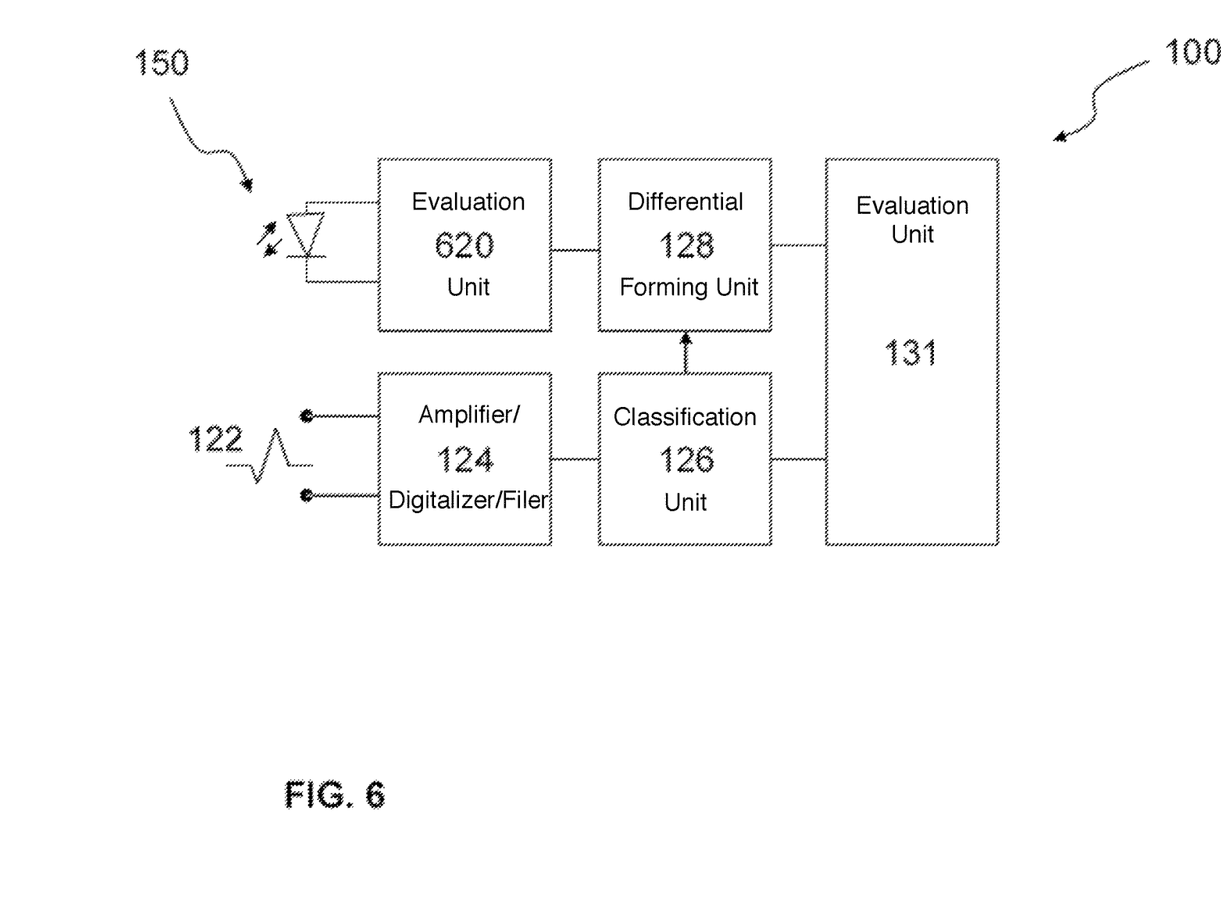
FIG. 6 shows a schematic illustration of a block diagram of a device including a sensor unit according to one or more embodiments of the invention.

FIG. 6 shows a block diagram of a device 100 with a sensor unit 150 according to one or more embodiments of the invention, such as an extraction rate sensor. In at least one embodiment, the sensor unit 150 may be formed as an oximeter sensor, for example as shown in FIGS. 1 to 3.

In one or more embodiments, the myocardial oxygen saturation may be continuously detected by the permanently implanted optical sensor unit 150 in a second evaluation unit 620 connected to the sensor. In at least one embodiment, the implant may be equipped with, or may include, an electrocardiogram/intracardiac electrogram (ECG/IEGM) electrode interface 122, wherein an ECG amplifier/digitalizer/filter 124 may derive the ECG signals of the heart in order to identify from these signals the individual cardiac cycles and phases thereof (systole start/diastole start, etc.) in a classification unit 126. In one or more embodiments, the phases of the heart cycle may be signaled to a differential forming unit 128 in order to detect the difference of the oxygen saturation within the individual cardiac cycles. In at least one embodiment, such information and the further cardiac states established by the classification unit 126 may be stored in the evaluation unit 131 and optionally may be evaluated as discussed above with respect to FIG. 5. In one or more embodiments, the data or information may be transferred to an external evaluation system.

By way of at least one embodiment, the second evaluation unit 620 may determine a critical point of the oxygen extraction rate from a course of the measured oxygen extraction over the heart rate, wherein the critical point includes one or more of when the oxygen extraction rate decreases with increasing heart rate, when the oxygen extraction rate with increasing heart rate transitions into a saturation range, and when the oxygen extraction rate with increasing heart rate transitions into a saturation range and at the same time the maximum oxygen saturation value decreases.

In one or more embodiments, the second evaluation unit 620 may be simultaneously connected to an electrode line (not illustrated) to sense the electrical activity of the heart in order to determine the cardiac cycle length.

By way of at least one embodiment of the invention, with an implantable sensor, the systolic myocardial oxygen saturation may be continuously monitored and the therapy requirements may be adapted accordingly in cardiac insufficiency patients.

Figure 7:
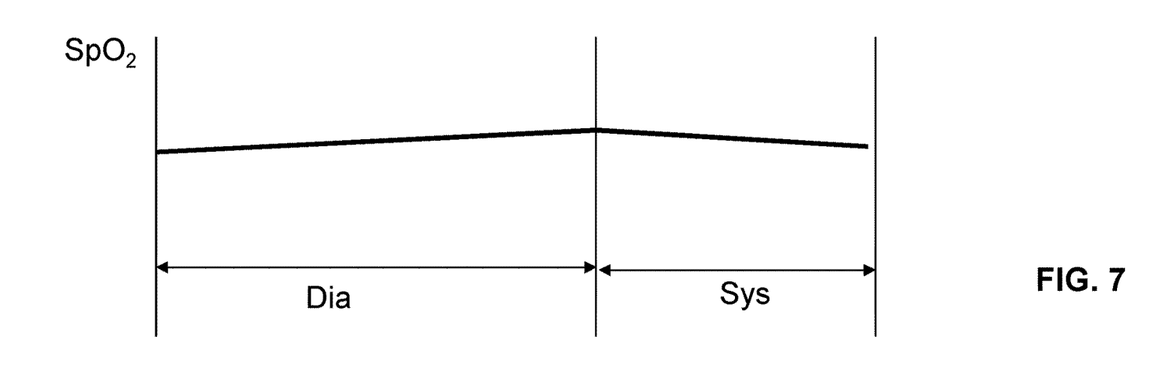
FIG. 7 shows a schematic illustration of a course of a myocardial oxygen saturation dependent from a contraction state in a non-hypoxic range.
Figure 8:
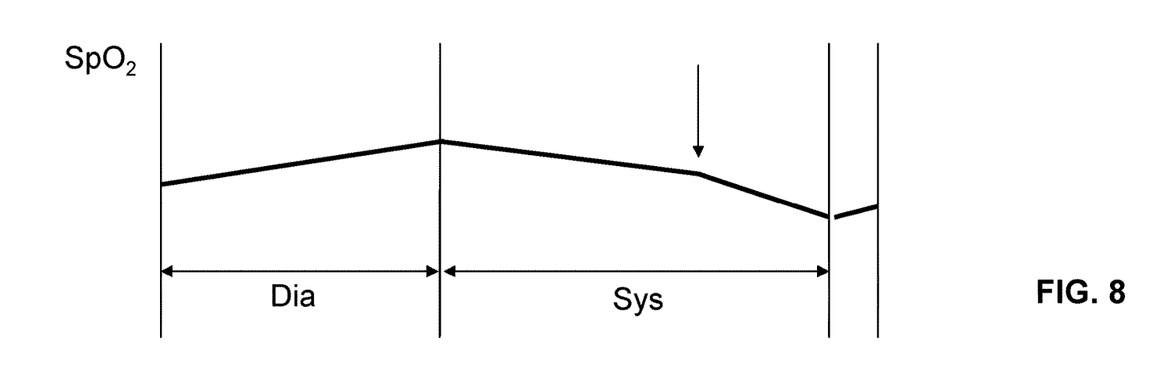
FIG. 8 shows a schematic illustration of a course of a myocardial oxygen saturation dependent from a contraction state in a hypoxic range.

FIG. 7 shows a course of a myocardial oxygen saturation $SpO_2$ depending on a contraction state of the heart in a non-hypoxic range, according to one or more embodiments of the invention. FIG. 8 shows a course of a myocardial oxygen saturation $SpO_2$ depending on a contraction state of the heart in a hypoxic range, according to one or more embodiments of the invention.

During the diastole Dia in FIG. 7, in at least one embodiment, the oxygen saturation $SpO_2$ tends to rise, since the perfusion overcompensates for the oxygen consumption in the myocardium. During the systole Sys, in one or more embodiments, more oxygen may be consumed than may be fed via the additionally limited perfusion. In at least one embodiment, the limitation of the perfusion may be caused by a compression of the small coronary arteries during the systole Sys and may increase with time and intensity of the contraction.

As shown in FIG. 8, according to one or more embodiments, a slight rise of the oxygen saturation $SpO_2$ during the diastole Dia may be seen. In at least one embodiment, the duration and intensity of the systole Sys may be increased with increased load, such that, following a moderate decrease of the oxygen saturation $SpO_2$ during the systole Sys in the end-systolic portion, an over-proportional decrease of the oxygen availability may be observed based on the extended contraction and further limited perfusion. In one or more embodiments, the transition is shown in FIG. 8 by a vertical arrow. In at least one embodiment, the drastic reduction of the oxygen saturation may be classified as myocardial hypoxia and may lead to a corresponding load restriction in cardiac insufficiency patients and later may lead to decompensation and accompanying cardiac function disruptions.

As such, one or more embodiments of the invention may identify excessive oxygen deficiency and may signal such excessive oxygen deficiency. In at least one embodiment, no absolute value measurement is necessary to monitor the progress, wherein a relative comparison within the cardiac cycle may be sufficient.

Figure 9:
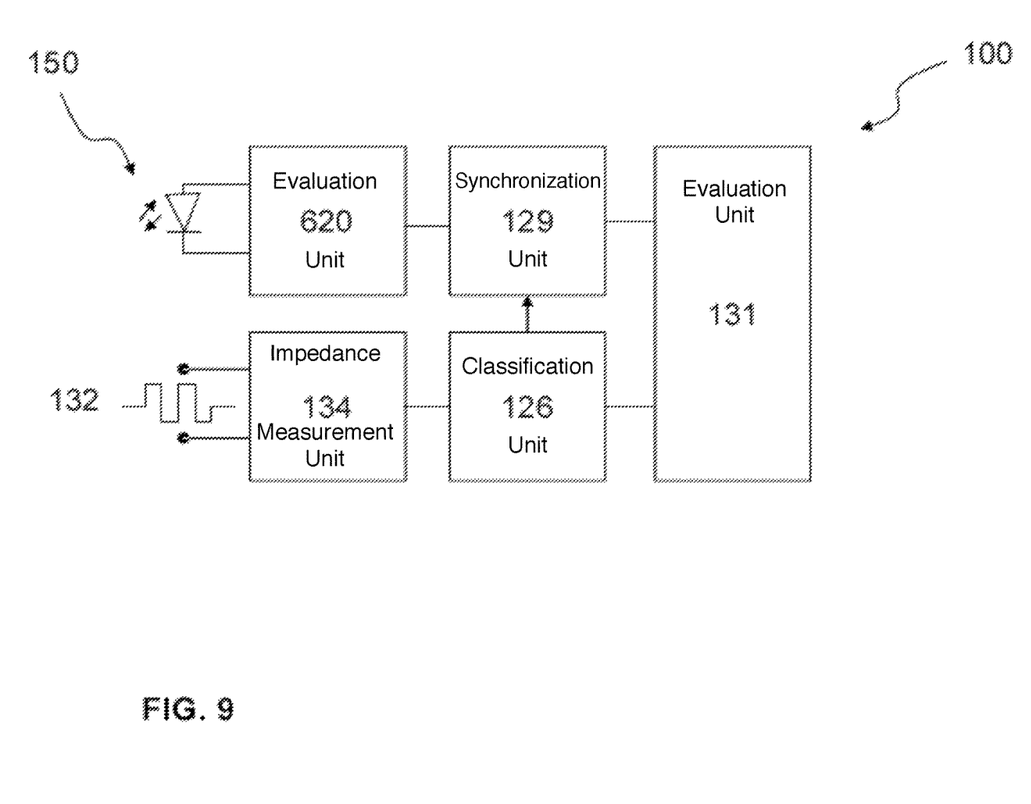
FIG. 9 shows a schematic illustration of a block diagram of a device including a sensor unit according to one or more embodiments of the invention.

FIG. 9 shows a block diagram of a device 100 with a sensor unit 150, according to one or more embodiments of the invention, that measure an oxygen extraction rate. In at least one embodiment, the sensor unit 150 may be formed as an oximeter sensor, for example as shown in FIGS. 1 to 3 and as discussed above.

In one or more embodiments, the myocardial oxygen saturation may be detected continuously by the permanently implanted optical sensor unit 150 in a second evaluation unit 620 connected to the sensor unit 150. In at least one embodiment, the implant may be equipped with or may include a mechanical contraction detection system 132. In one or more embodiments, using a unipolar, continuous impedance measurement 134, the mechanical contraction detection system 132 may detect the mechanical contraction state of the heart, for example by a principle derived from the closed loop stimulation or CLS, wherein the different conductivity of blood and myocardial tissue may be used in order to record the contraction state of the heart over a cardiac cycle. In at least one embodiment, during the diastole, there is a relatively large blood volume around the measurement electrode in the ventricle, and the measured impedance may be relatively low based on the improved conductivity of the blood. In one or more embodiments, during the systole, the influence of the surrounding myocardial tissue may increase and the impedance may rise. In at least one embodiment, CLS may be used to adapt the rate of pacemakers and implantable cardioverter defibrillators (ICDs), to mechanically determine from these signals the start and end of the contraction states in a classification unit 126. In one or more embodiments, the phases of the mechanical pumping function may be associated temporally with the oxygen saturation in a synchronization unit 129. In at least one embodiment, the oxygen course may then be evaluated in the evaluation unit 131 with respect to a hypoxia criterion, for example excessive decrease at the end of the systole in relation to the average oxygen value over the entire cardiac cycle, and may be signaled.

In at least one embodiment of the invention, in contrast to what is shown in FIG. 6, the device 100 shown in FIG. 9 may indicate the start of a reduced myocardial oxygen supply and may provide clinical intervention in a timely manner.

Figure 10:
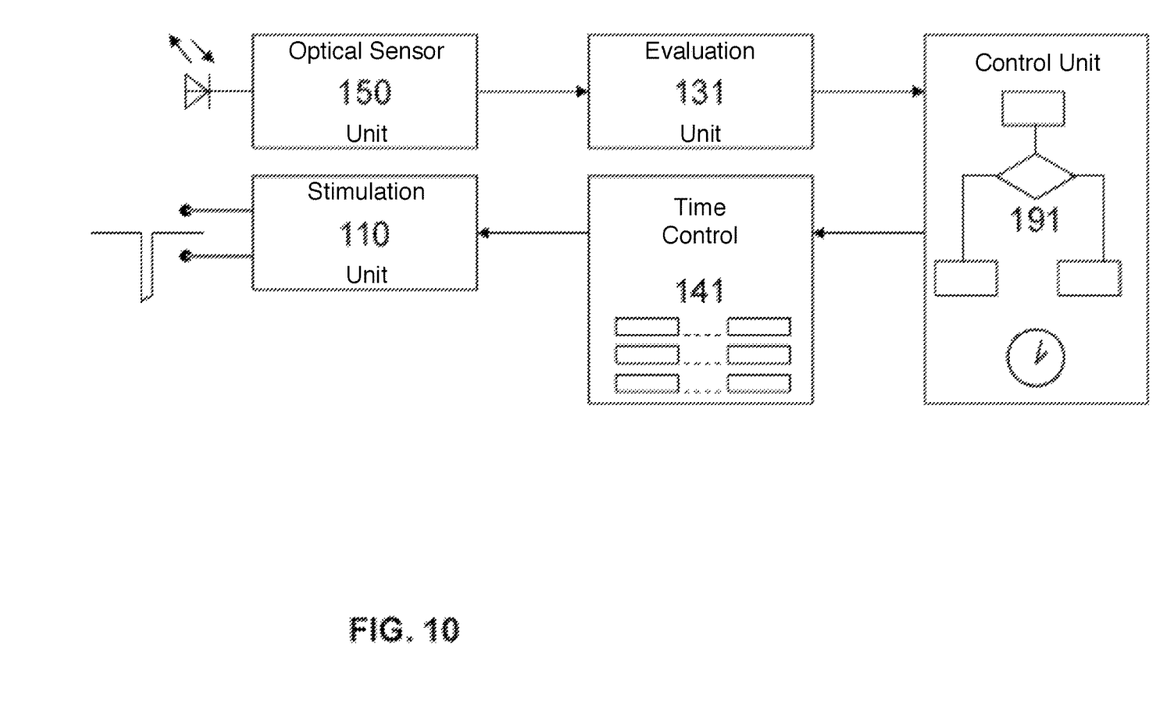
FIG. 10 shows a schematic illustration of a device including a sensor unit according to one or more embodiments of the invention.

FIG. 10 shows a block diagram of a cardiac assist system 200 with a sensor unit 150 according to one or more embodiments of the invention, which may be controlled in accordance with the myocardial oxygen saturation of the heart, the contraction state of the heart, and the cardiac rhythm.

In at least one embodiment, the cardiac assist system 200 may include a sensor unit 150, which may be formed as or may include an oximeter sensor, for example as shown in FIGS. 1 to 3 and as discussed above. In one or more embodiments, the sensor unit 150 may be equipped with or may include an ECG/IEGM electrode interface 122, wherein in an ECG/IEGM amplifier/digitalizer/filter 124 the sensor unit may derive the ECG/IEGM signals of the heart in order to identify the individual cardiac cycles and to determine the heart rate from these signals in a classification unit 126. In at least one embodiment, the sensor unit 150 may be equipped with or may include a mechanical contraction detection system 132. which In one or more embodiments, the mechanical contraction detection system 132 may detect the mechanical contraction state of the heart using a unipolar, continuous impedance measurement, for example based on closed loop stimulation or CLS, in order to determine from these signals the start and end of the mechanical contraction states in a classification unit 126. In at least one embodiment, the mechanical contraction detection system 132 may include one or more strain gauges, one or more pressure sensors, or one or more acceleration sensors. In one or more embodiments, the expanded sensor unit may continuously deliver the data concerning the myocardial oxygen saturation, the cardiac rhythm, and the contraction state of the heart to an evaluation unit 131. In at least one embodiment, the evaluation unit 131 may correlate the three data sources, including the data concerning the myocardial oxygen saturation, the cardiac rhythm, and the contraction state of the heart, with one another and may assign the measured oxygen saturation curves to the functional states of the cardiac cycle in a manner dependent on heart rate.

According to one or more embodiments, the cardiac assist system 200 may include a multi-channel cardiac stimulation unit 110. In at least one embodiment, the stimulation unit 110 may be connected to a time control 141, which provides a number of parameters, which are variable within programmable limits, to control timing during the stimulation (for example AV time, VV time, maximum heart rate/stimulation frequency, etc.). In one or more embodiments, the cardiac assist system 200 may include a control unit 191, which may start a test algorithm cyclically at programmable time intervals, wherein in each case the control unit 191 may vary one or more parameters of the time control 141 and therefrom evaluate the measurement curves of the myocardial oxygen saturation. In at least one embodiment, the optimal parameters of the time control 141 may be calculated based on the evaluation by stored algorithms in the control unit 191 for various states of load of the heart and may be used to carry out the next test algorithm in the time control 141. One or more embodiments of the invention may include additional sensor parameters concerning the metabolic needs of the patient or activity state thereof in the optimization of the parameters to control time, such that stimulation parameter sets adapted for various states of load may be provided.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A device configured to be inserted into a bodily tissue or in blood of a human or animal body, comprising:
   at least one permanently implantable sensor unit that detects a signal that represents an oxygen content along a measurement path,
      wherein said at least one permanently implantable sensor unit comprises a transmitter and a receiver;
   a reflector provided on the device, wherein said reflector is arranged in the measurement path between the transmitter and the receiver of the at least one permanently implantable sensor unit to reflect the signal; and,
   a fixation unit, wherein the reflector is arranged on or in said fixation unit configured to permanently fix the device to or in the bodily tissue.

2. The device as claimed in claim 1, further comprising an electrode line, wherein the at least one permanently implantable sensor unit is connected to said electrode line, wherein said electrode line is configured to sense electrical activity of a heart to determine cardiac cycle length, and wherein the signal that represents an oxygen content is determined for one or more of a cardiac cycle and phases of a cardiac cycle.

3. The device as claimed in claim 1, wherein the at least one permanently implantable sensor unit is configured to be coupled to one or more therapeutic implants.

4. The device according to claim 1, further comprising a therapy unit coupled to the at least one permanently implantable sensor unit.

5. The device as claimed in claim 1, further comprising a therapy unit, wherein the at least one permanently implantable sensor unit is part of the therapy unit, and wherein the therapy unit comprises one or more of at least one sensing electrode, a therapeutic stimulation electrode and a defibrillation electrode.

6. The device as claimed in claim 1, wherein the at least one permanently implantable sensor unit detects a pH value.

7. The device as claimed in claim 1, wherein the at least one permanently implantable sensor unit is coupled to a temperature sensor and a heating element.

8. The device as claimed in claim 1, wherein the at least one permanently implantable sensor unit is coupled to one or more of a strain gauge, a pressure sensor, an acceleration sensor and a temperature sensor that is configured to detect a contraction state of bodily tissue in a region of the measurement path.

9. The device as claimed in claim 1, wherein a maximum myocardial oxygen saturation, a minimum myocardial oxygen saturation, and a difference between minimum and maximum myocardial oxygen saturation are determined from the signal that represents an oxygen content, and therefrom an oxygen extraction rate of a heart is derived.

10. The device as claimed in claim 9, wherein the maximum myocardial oxygen saturation, the minimum myocardial oxygen saturation, and the difference between the minimum and the maximum myocardial oxygen saturation are determined over a cardiac cycle, and therefrom a course of the oxygen extraction rate is determined dependent from a heart rate.

11. The device as claimed in claim 10, wherein a critical point of the oxygen extraction rate is determined from the course of the oxygen extraction rate over the heart rate, wherein the critical point comprises one or more of when the oxygen extraction rate decreases with rising heart rate, when the oxygen extraction rate with rising heart rate transitions into a saturation range, and when the oxygen extraction rate with rising heart rate transitions into a saturation range and at the same time the maximum myocardial oxygen saturation decreases.

12. The device as claimed in claim 10, wherein a critical point of the oxygen extraction rate is determined, wherein said critical point comprises when a systolic oxygen saturation falls below a critical reference value or decrease rate of decrease of the oxygen extraction rate exceeds a critical value during the systole.

13. A cardiac assist system comprising:
   a device configured to be inserted into a bodily tissue or in blood of a human or animal body comprising
      at least one permanently implantable sensor unit that detects a signal that represents an oxygen content along a measurement path,
         wherein said at least one permanently implantable sensor unit comprises a transmitter and a receiver;
   at least one therapy unit;
   a control unit;
   a reflector provided on the device, wherein said reflector is arranged in the measurement path between the transmitter and the receiver of the at least one permanently implantable sensor unit to reflect the signal; and,
   a fixation unit, wherein the reflector is arranged on or in said fixation unit configured to permanently fix the device to or in the bodily tissue, and
   wherein the control unit is configured to optimize one or more of at least one stimulation parameter and at least one therapy parameter, such that an oxygen saturation in a region of the measurement path with respect to a defined state of load of a heart is set.

14. The cardiac assist system as claimed in claim 13, wherein the at least one permanently implantable sensor unit is coupled to one or more of a strain gauge, a pressure sensor, an acceleration sensor and a temperature sensor configured to detect a contraction state of the heart.

15. The cardiac assist system as claimed in claim 1, wherein a variable that represents the oxygen content is detected and correlated with a contraction state of the heart.

16. A method of determining an oxygen content in a bodily tissue or in blood of a human or animal body with a device configured to be inserted into the bodily tissue or in blood of a human or animal body, comprising:
- detecting a signal that represents an oxygen content in the bodily tissue or in the blood along a measurement path via at least one permanently implantable sensor unit of the device,
  - wherein said at least one permanently implantable sensor unit comprises a transmitter and a receiver;
- reflecting the signal by a reflector of the device,
  - wherein the reflector is provided on the device, and
  - wherein the reflector is arranged in the measurement path between the transmitter and the receiver of the at least one permanently implantable sensor unit;
- arranging the reflector on a fixation unit and permanently fixing the device to or in the bodily tissue via the fixation unit;
- detecting a variable that represents the oxygen content in the bodily tissue or in the blood at least over one cardiac cycle; and,
- correlating the variable with a contraction state of the heart.

* * * * *